United States Patent
Martin et al.

(10) Patent No.: US 7,829,073 B2
(45) Date of Patent: *Nov. 9, 2010

(54) ANHYDROUS COSMETIC COMPOSITIONS COMPRISING AT LEAST ONE POLYMERIC GELLING AGENT, AT LEAST ONE NON-VOLATILE OIL, AND POLY(METHYL METHACRYLATE) PARTICLES

(75) Inventors: Guenaelle Martin, Paris (FR); Agnès Themens, Bourg la Reine (FR)

(73) Assignee: L'Oreal S.A., Paris (FR)

( * ) Notice: Subject to any disclaimer, the term of this patent is extended or adjusted under 35 U.S.C. 154(b) by 1498 days.

This patent is subject to a terminal disclaimer.

(21) Appl. No.: 11/099,556

(22) Filed: Apr. 6, 2005

(65) Prior Publication Data

US 2005/0239950 A1 Oct. 27, 2005

Related U.S. Application Data

(60) Provisional application No. 60/569,629, filed on May 11, 2004.

(30) Foreign Application Priority Data

Apr. 6, 2004 (FR) .................................. 04 50695

(51) Int. Cl.
- A61K 31/74 (2006.01)
- A61Q 1/00 (2006.01)
- A61Q 1/02 (2006.01)
- A61Q 19/00 (2006.01)

(52) U.S. Cl. .............. 424/78.03; 424/70.16; 424/78.02; 424/78.06; 424/78.07; 424/64; 424/69; 424/401

(58) Field of Classification Search .................. 424/401, 424/69, 70.16, 78.02, 78.03, 78.06, 78.07, 424/64

See application file for complete search history.

(56) References Cited

U.S. PATENT DOCUMENTS

| | | | |
|---|---|---|---|
| 4,892,726 A * | 1/1990 | Yonekura et al. | ............... 424/63 |
| 5,030,446 A | 7/1991 | Russ et al. | |
| 5,221,534 A | 6/1993 | DesLauriers et al. | |
| 5,851,517 A | 12/1998 | Mougin et al. | |
| 6,395,301 B1 | 5/2002 | Cantin | |
| 2004/0096472 A1 | 5/2004 | Tournilhac | |
| 2004/0137028 A1 | 7/2004 | de la Poterie | |
| 2005/0238603 A1 * | 10/2005 | Themens et al. | ......... 424/70.11 |

FOREIGN PATENT DOCUMENTS

| | | |
|---|---|---|
| EP | 0 293 795 A1 | 12/1988 |
| EP | 0 749 747 B1 | 12/1996 |
| EP | 1 002 528 A1 | 5/2000 |
| FR | 2 787 995 | 7/2000 |
| FR | 2 840 204 A1 | 12/2003 |
| FR | 2 843 020 | 2/2004 |
| WO | WO 98/42298 | 10/1998 |

OTHER PUBLICATIONS http://web.archive.org/web/20020907182208/www.nihon-junyaku.co.jp/english/product/pdt02.html.*
French Search Report for FR 0404185, dated Nov. 15, 2004 (2 pages).
Restriction Requirement mailed Feb. 20, 2009, in U.S. Appl. No. 11/099,528.
French Search Report for FR 0450696 (French priority application for U.S. Appl. No. 11/099,528), dated Nov. 15, 2004.
English language abstract of FR 2 840 204 A1, Dec. 5, 2003.
Co-pending U.S. Appl. No. 11/099,528, filed Apr. 6, 2005.
Office Action mailed Nov. 9, 2009, in co-pending U.S. Appl. No. 11/099,528.

* cited by examiner

*Primary Examiner*—John Pak
(74) *Attorney, Agent, or Firm*—Finnegan, Henderson, Farabow, Garrett & Dunner, LLP

(57) ABSTRACT

The present disclosure relates to anhydrous compositions for making up or caring for the skin, for example foundations, comprising at least one liquid organic phase comprising at least one non-volatile oil, at least one amorphous gelling polymer formed by polymerization of an olefin, and poly (methyl methacrylate) particles, wherein the amount of the at least one non-volatile oil present in the composition is greater than the amount of poly(methyl methacrylate) particles present in the composition.

The compositions may exhibit a smooth and melting creamy texture, spread easily over the skin, and make it possible to obtain a homogeneous make-up that has a powdery and matt finish and that confers a pleasant softness on the skin. The make-up may also exhibit good properties of hold.

57 Claims, No Drawings

ANHYDROUS COSMETIC COMPOSITIONS COMPRISING AT LEAST ONE POLYMERIC GELLING AGENT, AT LEAST ONE NON-VOLATILE OIL, AND POLY(METHYL METHACRYLATE) PARTICLES

This application claims benefit of U.S. Provisional Application No. 60/569,629, filed May 11, 2004, and French Application No. 04 50695, filed Apr. 6, 2004, both of which are hereby incorporated by reference.

The present disclosure relates to anhydrous cosmetic compositions for making up or caring for skin. The present disclosure also relates to processes for making up or caring for human skin comprising applying the composition to the skin.

The compositions for making up the skin can be foundations, eye shadows, blushers, concealers, and products for making up the body. For example, the present disclosure relates to foundation compositions.

The care compositions can be, for example, make-up bases, mattifying products for the skin, and products for caring for skin.

For example, the compositions are those for making up skin.

Foundation compositions are commonly employed not only to give an attractive color to the skin, for example to the face, but also to conceal the imperfections of the skin, such as red blotches and blemishes.

These compositions may exhibit varied textures, ranging from fluid to solid, and generally comprise oils and pulverulent coloring materials. One of the difficulties encountered by users is that of being able to uniformly spread the foundation over the entire surface of the face, so as to uniformly distribute the product. Compositions with thick or solid textures may be difficult to spread because of their high viscosities. Compositions with fluid textures may not always be appropriate for producing a uniform make-up and not leaving visible marks on the skin, for example because of their poor spreading over the entire surface of the face to be made up. Furthermore, the presence of pulverulent materials can produce a desiccating effect on the make-up, resulting in a feeling of tightness, thus rendering the make-up uncomfortable to wear throughout the day.

Consumers are always searching for products that have innovative texture effects. For example, consumers seek products for making up or caring for skin that exhibit different textures before and after application.

Thus, it would be desirable to have make-up or care compositions that can have the appearance of a smooth cream and converted to a powdery finish after application to the skin. Also desirable would be compositions that may exhibit a feeling of softness when applied to the skin, that may exhibit good properties of hold, for example of hold with regard to sebum or sweat, such as after twelve hours following application of the composition, and/or that make it possible to obtain matte make-up or care compositions for the skin.

The present inventors have surprisingly discovered that such compositions may be obtained by combining at least one non-volatile oil, at least one specific polymeric gelling agent, and poly(methyl methacrylate) particles. More specifically, the present disclosure relates to anhydrous compositions for making up or caring for the skin, comprising at least one liquid organic phase comprising at least one non-volatile oil, at least one amorphous gelling polymer formed by polymerization of an olefin, and poly(methyl methacrylate) particles, the amount of the at least one non-volatile oil present in the composition being greater than the amount of poly(methyl methacrylate) particles present in the composition.

The compositions according to the present disclosure can exhibit a smooth creamy texture that melts when it is applied to the skin. The compositions can spread easily over the skin and make it possible to obtain a uniform make-up on the skin without leaving visible traces. Furthermore, after application to the skin, the made-up or deposited layer of the composition on the skin may exhibit a powdery and velvety finish and may be comfortable to wear, without a dry or tight feeling. Skin made-up or treated with the compositions according to the present disclosure may exhibit a pleasant softness and a matte appearance. Furthermore, the make-up obtained may have good properties of hold, for example of hold to sebum or to sweat. For instance, twelve hours after application of the composition, the make-up may still remain on the skin, may be homogeneous, and may also exhibit satisfactory matteness.

Another aspect of the present disclosure relates to cosmetic processes to make up or non-therapeutically treat skin, comprising applying, to the skin, compositions as defined above.

A further aspect of the present disclosure relates to the use of compositions as defined above to produce a make-up having good hold, for example lasting at least 12 hours, and/or a matte make-up and/or a soft made-up skin and/or a comfortable make-up and/or a make-up having a powdery appearance and/or a homogeneous make-up.

The term "anhydrous composition," as used herein, is understood to mean a composition comprising less than 2% by weight of water, for example less than 0.5% of water, and even a composition that is devoid of water, wherein any water present is not added during the preparation of the composition but is residual water introduced by the ingredients mixed.

The at least one polymeric gelling agent present in the compositions according to the present disclosure may be an amorphous polymer formed by polymerization of an olefin. The term "amorphous polymer," as used herein, is understood to mean a polymer that does not have a crystalline form. The olefin can be, for example, an elastomeric monomer comprising at least one ethylenic unsaturation.

Non-limiting mention may be made, as examples of olefins, of ethylenic carbon monomers comprising, for example, one or two ethylenic unsaturations and comprising from 2 to 5 carbon atoms, such as ethylene, propylene, butadiene, and isoprene.

The at least one polymeric gelling agent may be capable of thickening or gelling the organic phase of the composition. The polymeric gelling agent may also be film-forming, that is to say that it may be capable of forming a film when it is applied to the skin.

The at least one polymeric gelling agent may be chosen from, for example, diblock, triblock, multiblock, radial, and star copolymers, and mixtures thereof. In one embodiment, the at least one polymeric gelling agent may be chosen from, for example, triblock, multiblock, radial, and star copolymers, and mixtures thereof.

Examples of such polymeric gelling agents are disclosed, for instance, in U.S. patent application Publication No. US 2002/005562 and in U.S. Pat. No. 5,221,534.

In one embodiment, the polymeric gelling agent is an amorphous block copolymer of styrene and of olefin.

The at least one polymeric gelling agent may be, for example, hydrogenated in order to reduce the residual ethylenic unsaturations after the polymerization of the monomers.

For example, the at least one polymeric gelling agent may be an optionally hydrogenated copolymer comprising styrene blocks and ethylene/$C_3$-$C_4$ alkylene blocks.

Non-limiting mention may be made, as examples of hydrogenated diblock copolymers, of styrene-ethylene/propylene copolymers and styrene-ethylene/butadiene copolymers. Diblock polymers are sold, for example, under the name Kraton® G1701E by Kraton Polymers.

Non-limiting mention may be made, as examples of hydrogenated triblock copolymers, of styrene-ethylene/propylene-styrene copolymers, styrene-ethylene/butadiene-styrene copolymers, styrene-isoprene-styrene copolymers, and styrene-butadiene-styrene copolymers. Triblock polymers are sold, for example, under the names Kraton® G1650, Kraton® G1652, Kraton® D1101, Kraton® D1102, and Kraton® D1160 by Kraton Polymers.

Blends of hydrogenated styrene-butylene/ethylene-styrene triblock copolymers and of hydrogenated ethylene-propylene-styrene star polymers, such blends being, for example, in isododecane, may also be used as polymeric gelling agents in the compositions according to the present disclosure. Such blends are sold, for example, by Penreco under the trade names Versagel® M5960 and Versagel® M5670.

In one embodiment, the compositions according to the present disclosure comprise, as a polymeric gelling agent, a diblock copolymer such as those described above, for example a styrene-ethylene/propylene diblock copolymer.

The polymeric gelling agent may be present in the compositions according to the present disclosure in an amount ranging from 0.1% to 10% by weight, for example from 0.5% to 5% by weight, such as from 1% to 3% by weight, relative to the total weight of the composition.

The compositions according to the present disclosure comprise at least one non-volatile oil.

The term "non-volatile oil," as used herein, is understood to mean an oil that remains on the skin at ambient temperature and atmospheric pressure for at least several hours and that has, for example, a vapour pressure of less than 0.13 Pa (0.001 mmHg).

The at least one non-volatile oil may be chosen from hydrocarbon oils, for example those of animal and vegetable origin, silicone oils, and their mixtures. The term "hydrocarbon oil," as used herein, is understood to mean an oil comprising mainly hydrogen and carbon atoms, and optionally oxygen, nitrogen, sulfur, and/or phosphorus atoms.

The at least one non-volatile oil may be chosen, for example, from optionally fluorinated non-volatile hydrocarbon oils and/or non-volatile silicone oils.

Non-limiting mention may be made, as examples of non-volatile hydrocarbon oils, of:

hydrocarbon oils of animal origin;
hydrocarbon oils of vegetable origin, such as triglycerides comprising esters of fatty acids and glycerol, wherein the fatty acids can have various chain lengths ranging from $C_4$ to $C_{24}$, and wherein these chains may be linear or branched and saturated or unsaturated; non-limiting examples of these oils include triglycerides of heptanoic acid and triglycerides of octanoic acid; wheat germ, sunflower, grape seed, sesame, corn, apricot, castor, karite, avocado, olive, soybean, sweet almond, palm, rapeseed, cottonseed, hazelnut, macadamia, jojoba, alfalfa, poppy, pumpkinseed, cucumber, blackcurrant seed, evening primrose, millet, barley, quinoa, rye, safflower, candlenut, passionflower, and musk rose oil; karite butter; and triglycerides of caprylic/capric acids, such as those sold by Stéarineries Dubois and those sold under the names Miglyol 810®, 812®, and 818® by Dynamit Nobel;
synthetic ethers comprising from 10 to 40 carbon atoms;
linear and branched hydrocarbons of mineral and synthetic origin, such as liquid petrolatum, polydecenes, hydrogenated polyisobutene, such as Parleam®, squalane, liquid paraffins, and their mixtures;
synthetic esters, such as oils of formula $R_1COOR_2$, wherein $R_1$ is chosen from linear and branched fatty acid radicals comprising from 1 to 40 carbon atoms, and $R_2$ is chosen from hydrocarbon chains, for example branched hydrocarbon chains, comprising from 1 to 40 carbon atoms, provided that the sum of the carbon atoms in $R_1$ and $R_2$ is greater than or equal to 10; non-limiting examples of these esters include Purcellin oil (cetearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, heptanoates, octanoates, decanoates, and ricinoleates of alcohols and of polyalcohols, such as propylene glycol dioctanoate; hydroxylated esters, such as isostearyl lactate, diisostearyl malate, and 2-octyidodecyl lactate; and polyol esters and pentaerythritol esters;
fatty alcohols that are liquid at ambient temperature and that comprise a branched and/or unsaturated carbon chain comprising from 12 to 26 carbon atoms, such as octyldodecanol, isostearyl alcohol, oleyl alcohol, 2-hexyldecanol, 2-butyloctanol, and 2-undecylpentadecanol;
higher fatty acids, such as oleic acid, linoleic acid, linolenic acid, and their mixtures.

Non-limiting examples of non-volatile silicone oils that may be used in the compositions according to the present disclosure include non-volatile polydimethylsiloxanes (PDMSs), polydimethylsiloxanes comprising pendant alkyl or alkoxy groups and/or alkyl or alkoxy groups at the end of the silicone chain, wherein the groups each have from 2 to 24 carbon atoms, and phenylated silicones, such as phenyl trimethicones, phenyl dimethicones, phenyl(trimethylsiloxy) diphenylsiloxanes, diphenyl dimethicones, and diphenyl(methyldiphenyl)trisiloxanes, and their mixtures.

For example, the at least one non-volatile oil can be chosen from $C_{12}$-$C_{36}$ esters, such as those described above.

The at least one non-volatile oil can be present in the compositions according to the present disclosure in an amount ranging from 0.5% to 60% by weight, for example from 1% to 50% by weight, such as from 5% to 40% by weight, for instance from 5% to 30% by weight, such as from 10% to 20% by weight, relative to the total weight of the composition.

The compositions according to the present disclosure may further comprise at least one volatile oil.

The term "volatile oil", within the meaning of the present disclosure, is understood to mean any oil capable of evaporating on contact with the skin at ambient temperature and atmospheric pressure. The at least one volatile oil according to the present disclosure may be chosen from volatile cosmetic oils that are liquid at ambient temperature and that have a non-zero vapor pressure at ambient temperature and atmospheric pressure. The vapour pressure may range, for example, from 0.13 Pa to 40 000 Pa (0.001 to 300 mmHg), such as from 1.3 to 1300 Pa (0.01 to 10 mmHg).

The at least one volatile oil can be chosen from volatile hydrocarbon oils, volatile silicone oils, volatile fluorinated oils, and their mixtures.

The at least one volatile hydrocarbon oil may be chosen from hydrocarbon oils comprising from 8 to 16 carbon atoms, for example branched $C_8$-$C_{16}$ alkanes, such as $C_8$-$C_{16}$ isoalkanes of petroleum origin (also referred to as isoparaffins), for instance isododecane (also referred to as 2,2,4,4,6-pentamethylheptane), isodecane, isohexadecane, and, for example, the oils sold under the trade names Isopars® and Permethyls®.

Further non-limiting examples of volatile oils that may be used in compositions according to the present disclosure include volatile silicones, such as volatile linear and cyclic silicone oils, for instance those that have a viscosity of less than or equal to 5 centistokes ($5\times10^{-6}$ m$^2$/s) and that comprise, for example, from 2 to 10 silicon atoms, such as from 2 to 7 silicon atoms. These silicones optionally comprise alkyl or alkoxy groups comprising from 1 to 10 carbon atoms. Non-limiting mention may be made, among the volatile silicone oils that can be used in the compositions according to the present disclosure, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and their mixtures.

Volatile fluorinated oils generally do not have a flash point.

Non-limiting mention may be made, as examples of volatile fluorinated oils, of nonafluoroethoxybutane, nonafluoromethoxybutane, decafluoropentane, tetradecafluorohexane, dodecafluoropentane, and their mixtures.

In one embodiment, the compositions according to the present disclosure comprise at least one volatile hydrocarbon oil, for example a mixture of isododecane and of isohexadecane.

The at least one volatile oil can be present in the compositions according to the present disclosure in an amount ranging from 5% to 60% by weight, for example from 10% to 55% by weight, such as from 20% to 50% by weight, for instance from 30% to 50% by weight, relative to the total weight of the composition.

The compositions according to the present disclosure also comprise poly(methyl methacrylate) particles. In one embodiment, these particles are not film-forming, that is to say that they do not form a continuous film when they are deposited on a substrate such as the skin.

The powders formed of poly(methyl methacrylate) are generally provided in the form of white-colored hollow or solid spherical particles, the number-average size of which is generally on the scale of a micrometer, for example varying from 3 to 15 microns, such as from 3 to 10 microns. The term "number-average size," as used herein, is understood to mean the dimension given by the random particle size distribution at half the population, referred to as D50.

It is also possible to characterize these poly(methyl methacrylate) particles by their density. For example, the density may vary according to the size of the spherical cavity of the particles. In the context of the present disclosure, this density may be assessed according to the following protocol referred to as packed density:

Powder, w=40 g, is poured into a graduated measuring cylinder. The measuring cylinder is then placed on a STAV 2003 device from Stampf Volumeter. The measuring cylinder is subsequently subjected to 1500 packing motions. The final volume Vf of packed powder is then measured directly on the measuring cylinder. The packed density is determined by the ratio w/Vf, in this example 40/Vf (Vf being expressed in cm$^3$ and w in g).

For example, the density of the poly(methyl methacrylate) particles that can be used according to the present disclosure can vary from 0.3 to 1.5, such as from 0.5 to 1.5, for instance from 1 to 1.5.

Non-limiting mention may be made, as examples of the poly(methyl methacrylate) particles suitable for use in the compositions according to the present disclosure, of the poly(methyl methacrylate) particles sold by Matsumoto Yushi Co. under the name "Micropearl M100", by LCW under the name "Covabead LH85," and by Nihon Junyaku under the name "Jurymer MB1".

The poly(methyl methacrylate) particles can be present in the compositions according to the present disclosure in an amount ranging from 0.5% to 30% by weight, for example from 0.5% to 25% by weight, such as from 1% to 20% by weight, for instance from 5% to 15% by weight, relative to the total weight of the composition.

The amount of the at least one non-volatile oil and of poly(methyl methacrylate) particles present in the compositions according to the present disclosure may be adjusted so that the amount of the at least one non-volatile oil present in the composition is greater than the amount of poly(methyl methacrylate) particles present in the composition. For example, these amounts are such that the at least one non-volatile oil/poly(methyl methacrylate) particles ratio by weight may be greater than or equal to 1, for instance ranging from 1 to 35, such as from 1 to 25, for example from 1 to 15. As a further example, the at least one non-volatile oil/poly(methyl methacrylate) particles ratio by weight may be greater than or equal to 1.5, for instance ranging from 1.5 to 35, such as from 1.5 to 25, for example from 1.5 to 15.

The compositions according to the present disclosure can further comprise at least one coloring material, chosen, for example, from pigments, pearlescent agents, fat-soluble dyes, and their mixtures.

The term "pigments," as used herein, is understood to mean white and colored, inorganic and organic particles of any shape that are insoluble in a physiological medium and that are intended to color the compositions according to the present disclosure.

The term "pearlescent agents," as used herein, is understood to mean iridescent particles of any shape produced, for example, by certain shellfish in their shells or else synthesized.

The term "dyes," as used herein, is understood to mean compounds, generally organic compounds, that are soluble in fatty substances, such as oils.

Pigments can be white and colored, and inorganic and organic. Non-limiting mention may be made, among inorganic pigments, of titanium dioxide, optionally surface-treated; zirconium and cerium oxides; zinc, iron (black, yellow, and red), and chromium oxides; manganese violet; ultramarine blue; chromium hydrate and ferric blue; and metal powders, such as aluminium powder and copper powder.

Non-limiting mention may be made, among organic pigments, of carbon black, pigments of D & C type, and lakes, based on cochineal carmine, of barium, strontium, calcium, and aluminium.

Pearlescent pigments can be chosen from white pearlescent pigments, such as mica covered with titanium oxide or with bismuth oxychloride; colored pearlescent pigments, such as titanium oxide-coated mica covered with iron oxides, titanium oxide-coated mica covered with, for example, ferric blue or chromium oxide, and titanium oxide-coated mica covered with an organic pigment of the abovementioned type; and pearlescent pigments based on bismuth oxychloride.

Non-limiting examples of fat-soluble dyes include, for example, Sudan red, D & C Red No. 17, D & C Green No. 6, β-carotene, soybean oil, Sudan brown, D & C Yellow No. 11, D & C Violet No. 2, D & C Orange No. 5, quinoline yellow, annatto, and bromoacids.

The at least one coloring material can be present in the compositions according to the present disclosure in an amount ranging from 0.1% to 30% by weight, for example from 0.1% to 20% by weight, such as from 0.5% to 15% by weight, for instance from 1% to 15% by weight, for example from 5% to 15% by weight, relative to the total weight of the composition.

The compositions according to the present disclosure can also further comprise at least one additional filler other than the poly(methyl methacrylate) particles described above.

The term "fillers," as used herein, is understood to mean colorless and white, inorganic and synthetic particles of any shape that are insoluble in the medium of the compositions, regardless of the temperature at which the compositions are manufactured.

The at least one additional filler can be inorganic or organic, of any shape, for example platelet-shaped, spherical or oblong, and of any crystallographic form (for example sheet, cubic, hexagonal, orthorhombic, and the like). Non-limiting mention may be made of talc, mica, silica, kaolin, polyamide (Nylon®) powders, poly-β-alanine powders, polyethylene powders, polyurethane powders, such as the powder formed of hexamethylene diisocyanate and trimethylol hexyllactone copolymer sold under the name Plastic Powder D-400 by Toshiki, the powders formed of tetrafluoroethylene polymers (Teflon®), lauroyllysine, starch, boron nitride, polymeric hollow microspheres, such as those of poly(vinylidene chloride)/acrylonitrile, for example Expancel® (Nobel Industrie), or of acrylic acid copolymers, silicone resin powders such as silsesquioxane powders (silicone resin powders disclosed, for example, in European Patent Application No. EP 293,795, and sold, for example, under the name Tospearls® from Toshiba), polyorganosiloxane elastomer particles, precipitated calcium carbonate, magnesium carbonate, basic magnesium carbonate, hydroxyapatite, hollow silica microspheres, glass microcapsules, ceramic microcapsules, metal soaps derived from organic carboxylic acids comprising from 8 to 22 carbon atoms, such as from 12 to 18 carbon atoms, for example zinc stearate, magnesium stearate, lithium stearate, zinc laurate, and magnesium myristate, and their mixtures.

The at least one additional filler can be present in the compositions according to the present disclosure in an amount ranging from 0.1% to 35% by weight, for example from 0.5% to 30% by weight, such as from 1% to 25% by weight, relative to the total weight of the composition.

For example, the at least one additional filler may be chosen from polyurethane powders, such as the powders formed of hexamethylene diisocyanate and trimethylol hexyllactone copolymer sold under the names "Plastic Powder D-400" and "Plastic Powder D-800" by Toshiki, and the polyurethane powder sold under the name "Plastic Powder CS-400" by Toshiki, silsesquioxane powders, talc, polyamide (Nylon®) powders, and their mixtures.

In one embodiment, the polyurethane powder is not film-forming, that is to say that it does not form a continuous film when it is deposited on a substrate such as the skin.

For example, the compositions according to the present disclosure can comprise a polyurethane powder as described above in an amount ranging from 0.5% to 30% by weight, for instance from 1% to 15% by weight, such as from 5% to 15% by weight, relative to the total weight of the composition.

As another example, the compositions according to the present disclosure can comprise a silsesquioxane powder in an amount ranging from 0.5% to 30% by weight, for instance from 1% to 15% by weight, such as from 1% to 10% by weight, relative to the total weight of the composition.

As yet another example, the compositions according to the present disclosure can comprise talc in an amount ranging from 0.1% to 30% by weight, for instance from 1% to 15% by weight, such as from 1% to 10% by weight, relative to the total weight of the composition.

The compositions can comprise, for example, polyamide powder in an amount ranging from 0.5% to 30% by weight, for instance from 1% to 15% by weight, such as from 1% to 10% by weight, relative to the total weight of the composition.

For example, the compositions according to the present disclosure can comprise a total amount of pulverulent materials ranging from 20% to 50% by weight, for instance from 25% to 45% by weight, such as from 30% to 40% by weight, relative to the total weight of the composition.

The compositions can further comprise at least one inorganic thickener for an oily phase, such as organophilic clay and pyrogenic silicas.

Organophilic clays are clays modified by chemical compounds that render the clay capable of swelling in oily media.

These clays are well-known products, and are described, for example, in the work "Minéralogie des argiles [Mineralogy of Clays], by S. Caillère, S. Hénin, and M. Rautureau, 2nd edition, 1982, Masson", the contents of which are hereby incorporated by reference.

These clays may be silicates comprising a cation, which can be chosen from calcium, magnesium, aluminium, sodium, potassium, and lithium cations, and their mixtures.

Non-limiting mention may be made, as examples of such products, of clays of the family of the smectites, such as montmorillonites, hectorites, bentonites, beidellites, and saponites, and of the family of the vermiculites, stevensite, and chlorites.

Clays that may be used in compositions according to the present disclosure can be of natural or synthetic origin. For example, clays that are cosmetically compatible and acceptable with keratinous substances, such as the skin, may be used.

The organophilic clays can be chosen from montmorillonite, bentonite, hectorite, attapulgite, sepiolite, and their mixtures. In one embodiment, the clay is a bentonite or a hectorite.

These clays can be modified with a chemical compound chosen from quaternary ammoniums, tertiary amines, amine acetates, imidazolines, amine soaps, fatty sulfates, alkylarylsulfonates, amine oxides, and their mixtures.

Non-limiting mention may be made, as examples of organophilic clays that may be used in compositions according to the present disclosure, of quaternary-18 bentonites, such as those sold under the names Bentone 3, Bentone 38, and Bentone 38V by Rheox, Tixogel VP by United Catalyst, and Claytone 34, Claytone 40, and Claytone XL by Southern Clay; stearalkonium bentonites, such as those sold under the names Bentone 27 by Rheox, Tixogel LG by United Catalyst, and Claytone AF and Claytone APA by Southern Clay; and quaternium-18/benzalkonium bentonites, such as those sold under the names Claytone HT and Claytone PS by Southern Clay.

Pyrogenic silicas can be obtained by high temperature hydrolysis of a volatile silicon compound in an oxyhydrogen flame, producing finely divided silicas. This process makes it possible to obtain, for example, hydrophilic silicas that exhibit a large number of silanol groups at their surfaces. Such hydrophilic silicas are sold, for example, under the names "Aerosil 130®", "Aerosil 200®", "Aerosil 255®", "Aerosil 300®", and "Aerosil 380®" by Degussa, and "Cab- O-Sil HS-5®", "Cab-O-Sil EH-5®", "Cab-O-Sil LM-130®", "Cab-O-Sil MS-55®", and "Cab-O-Sil M-5®" by Cabot.

The surface of silica may be chemically modified by a chemical reaction that generates a decrease in the number of silanol groups. For example, silanol groups may be substituted by hydrophobic groups: a hydrophobic silica is then obtained.

Examples of hydrophobic groups that may be substituted include:

trimethylsiloxyl groups, which are obtained, for example, by treatment of pyrogenic silica in the presence of hexamethyidisilazane. Silicas that are treated in this manner are called "Silica silylate," according to the CTFA (6th edition, 1995). They are sold, for example, under the names "Aerosil R812®" by Degussa and "Cab-O-Sil TS-530®" by Cabot.

dimethylsilyloxyl and polydimethylsiloxane groups, which are obtained, for example, by treatment of pyrogenic silica in the presence of polydimethylsiloxane or of dimethyidichlorosilane. Silicas that are treated in this manner are called "Silica dimethyl silylate," according to the CTFA (6th edition, 1995). They are sold, for example, under the names "Aerosil R972®" and "Aerosil R974®" by Degussa, and "Cab-O-Sil TS-6100®" and "Cab-O-Sil TS-720®" by Cabot.

Pyrogenic silicas exhibit, for example, a particle size on the order of nanometers to micrometers, for instance ranging from approximately 5 to 200 nm.

The at least one inorganic thickener for an oily phase can be present in the compositions according to the present disclosure in an amount ranging from 0.5% to 5% by weight, for example from 1% to 4% by weight, such as from 2% to 4% by weight, relative to the total weight of the composition.

The compositions according to the present disclosure can further comprise at least one conventional cosmetic ingredient that can be chosen, for example, from antioxidants, fragrances, preservatives, neutralizing agents, surfactants, waxes, sunscreen agents, vitamins, moisturizing agents, self-tanning compounds, and antiwrinkle active principles.

Needless to say, a person skilled in the art will take care to choose this or these optional additional compounds and/or their amounts so that the beneficial properties of the compositions according to the present disclosure are not, or not substantially, detrimentally affected by the addition.

In one embodiment, the composition is provided in the form of a deformable non-fluid gel, wherein the composition does not flow under its own weight at 25° C. in less than 5 minutes but can be deformed by simple crushing when the composition is taken up with the fingers. By contrast, a solid composition does not deform when it is brought into simple contact with the fingers.

The present disclosure may be understood more clearly with the aid of the non-limiting examples that follow, which constitute various embodiments of the compositions according to the present disclosure. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

EXAMPLE 1

A foundation of the following composition was prepared:

| | |
|---|---|
| Isononyl isononanoate | 15.7 g |
| Isododecane | 11.75 g |
| Isohexadecane | 14.1 g |
| Sorbitan monoisostearate | 1.5 g |
| Styrene-ethylene/propylene copolymer, sold under the name Kraton ® G 1701 E by Kraton Polymers | 2.5 g |
| Quaternary-18 hectorite gel, sold under the name "Bentone gel SS 71 V" by Elementis | 17.65 g |
| Polyurethane powder, sold under the name "Plastic Powder D-400" by Toshiki | 8 g |
| Poly(methyl methacrylate) powder | 9 g |
| Polymethylsilsesquioxane powder, sold under the name "Tospearl ® 145-A" by GE Toshiba Silicones | 1.25 g |
| Talc | 5.5 g |
| Pyrogenic silica, sold under the name "Aerosil ® 200" by Degussa | 1.8 g |
| Nylon powder | 2.75 g |
| Pigments | 8 g |
| Preservatives | 0.5 g |

This foundation exhibited a smooth creamy texture that melted when it was applied to the skin. It spread easily over the skin and made it possible to obtain a homogeneous make-up of the skin with a matt appearance, that had a powdery finish, and left the skin very soft. 12 hours after application, the make-up exhibited good hold to sebum and to sweat.

What is claimed is:

1. An anhydrous composition for making up or caring for the skin, comprising
   at least one liquid organic phase comprising at least one non-volatile oil,
   at least one amorphous gelling polymer formed by polymerization of an olefin, and poly(methyl methacrylate) particles,
wherein the amount of the at least one non-volatile oil present in the composition is greater than the amount of poly(methyl methacrylate) particles present in the composition.

2. The anhydrous composition according to claim 1, wherein the at least one amorphous gelling polymer is an amorphous block copolymer of styrene and of olefin.

3. The anhydrous composition according to claim 1, wherein the at least one amorphous gelling polymer is formed by polymerization of ethylenic carbon monomers.

4. The anhydrous composition according to claim 3, wherein said ethylenic carbon monomers comprise one or two ethylenic unsaturations and from 2 to 5 carbon atoms.

5. The anhydrous composition according to claim 1, wherein the at least one amorphous gelling polymer is formed by polymerization of an olefin chosen from ethylene, propylene, butadiene, and isoprene.

6. The anhydrous composition according to claim 1, wherein the at least one amorphous gelling polymer is chosen from diblock, triblock, multiblock, radial, and star copolymers, and mixtures thereof.

7. The anhydrous composition according claim 6, wherein the at least one amorphous gelling polymer is chosen from triblock, multiblock, radial, and star copolymers, and mixtures thereof.

8. The anhydrous composition according to claim 1, wherein the at least one amorphous gelling polymer is an optionally hydrogenated copolymer comprising styrene and ethylene/$C_3$-$C_4$ alkylene blocks.

9. The anhydrous composition according to claim 8, wherein the at least one amorphous gelling polymer is a hydrogenated diblock copolymer chosen from styrene-ethylene/propylene and styrene-ethylene/butadiene copolymers.

10. The anhydrous composition according to claim 8, wherein the at least one amorphous gelling polymer is a hydrogenated triblock copolymer chosen from styrene-ethylene/propylene-styrene copolymers, styrene-ethylene/butadiene-styrene copolymers, styrene-isoprene-styrene copolymers, and styrene-butadiene-styrene copolymers.

11. The anhydrous composition according to claim 1, wherein the at least one amorphous gelling polymer is a blend of hydrogenated styrene-butylene/ethylene-styrene triblock copolymer and of hydrogenated styrene-propylene-styrene star polymer.

12. The anhydrous composition according to claim 1, wherein the at least one amorphous gelling polymer is present in an amount ranging from 0.1% to 10% by weight, relative to the total weight of the composition.

13. The anhydrous composition according to claim 12, wherein the at least one amorphous gelling polymer is present in an amount ranging from 1% to 3% by weight, relative to the total weight of the composition.

14. The anhydrous composition according to claim 1, wherein the at least one non-volatile oil is chosen from non-volatile hydrocarbon oils, non-volatile silicone oils, and their mixtures.

15. The anhydrous composition according to claim 1, wherein the at least one non-volatile oil is chosen from $C_{12}$-$C_{36}$ esters.

16. The anhydrous composition according to claim 1, wherein the at least one non-volatile oil is present in an amount ranging from 0.5% to 60% by weight, relative to the total weight of the composition.

17. The anhydrous composition according to claim 16, wherein the at least one non-volatile oil is present in an amount ranging from 10% to 20% by weight, relative to the total weight of the composition.

18. The anhydrous composition according to claim 1, wherein the poly(methyl methacrylate) particles are present in an amount ranging from 0.5% to 30% by weight, relative to the total weight of the composition.

19. The anhydrous composition according to claim 18, wherein the poly(methyl methacrylate) particles are present in an amount ranging from 5% to 15% by weight, relative to the total weight of the composition.

20. The anhydrous composition according to claim 1, wherein the at least one non-volatile oil and the poly(methyl methacrylate) particles are present in an amount such that the ratio of the at least one non-volatile oil to the poly(methyl methacrylate) particles by weight is greater than 1:1.

21. The anhydrous composition according to claim 20, wherein the at least one non-volatile oil and the poly(methyl methacrylate) particles are present in an amount such that the ratio of the at least one non-volatile oil to the poly(methyl methacrylate) particles by weight ranges from greater than 1:1 to less than or equal to 15:1.

22. The anhydrous composition according to claim 1, wherein the at least one non-volatile oil and the poly(methyl methacrylate) particles are present in an amount such that the ratio of the at least one non-volatile oil to the poly(methyl methacrylate) particles by weight is greater than or equal to 1.5:1.

23. The anhydrous composition according to claim 22, wherein the at least one non-volatile oil and the poly(methyl methacrylate) particles are present in an amount such that the ratio of the at least one non-volatile oil to the poly(methyl methacrylate) particles by weight ranges from 1.5:1 to 15:1.

24. The anhydrous composition according to claim 1, further comprising at least one volatile oil.

25. The anhydrous composition according to claim 24, wherein the at least one volatile oil is chosen from volatile hydrocarbon oils.

26. The anhydrous composition according to claim 25, wherein the at least one volatile oil is chosen from volatile hydrocarbon oils comprising from 8 to 16 carbon atoms, and mixtures thereof.

27. The anhydrous composition according to claim 26, wherein the at least one volatile oil is chosen from isododecane, isodecane, isohexadecane, and mixtures thereof.

28. The anhydrous composition according to claim 27, wherein the at least one volatile oil is a mixture of isododecane and of isohexadecane.

29. The anhydrous composition according to claim 24, wherein the at least one volatile oil is chosen from volatile silicone oils.

30. The anhydrous composition according to claim 29, wherein the at least one volatile oil is chosen from octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

31. The anhydrous composition according to claim 24, wherein the at least one volatile oil is present in an amount ranging from 5% to 60% by weight, relative to the total weight of the composition.

32. The anhydrous composition according to claim 31, wherein the at least one volatile oil is present in an amount ranging from 30% to 50% by weight, relative to the total weight of the composition.

33. The anhydrous composition according to claim 1, further comprising at least one coloring material.

34. The anhydrous composition according to claim 33, wherein the at least one coloring material is chosen from pigments, pearlescent agents, fat-soluble dyes, and mixtures thereof.

35. The anhydrous composition according to claim 33, wherein the at least one coloring material is present in an amount ranging from 0.1% to 30% by weight, relative to the total weight of the composition.

36. The anhydrous composition according to claim 35, wherein the at least one coloring material is present in an amount ranging from 5% to 15% by weight, relative to the total weight of the composition.

37. The anhydrous composition according to claim 1, further comprising at least one additional filler other than the poly(methyl methacrylate) particles.

38. The anhydrous composition according to claim 37, wherein the at least one additional filler is chosen from talc, mica, silica, kaolin, polyamide powders, poly-β-alanine powders, polyethylene powders, polyurethane powders, powders formed of tetrafluoroethylene polymers, lauroyllysine, starch, boron nitride, hollow microspheres formed of poly(vinylidene chloride)/acrylonitrile, hollow microspheres formed of acrylic acid copolymers, silicone resin powders, polyorganosiloxane elastomer particles, precipitated calcium carbonate, magnesium carbonate, basic magnesium carbonate, hydroxyapatite, hollow silica microspheres, glass microcapsules, ceramic microcapsules, metal soaps derived from organic carboxylic acids comprising from 8 to 22 carbon atoms, and mixtures thereof.

39. The anhydrous composition according to claim 38, wherein the at least one additional filler is chosen from polyurethane powders, silsesquioxane powders, talc, silica, polyamide powders, and mixtures thereof.

40. The anhydrous composition according to claim 37, wherein the at least one additional filler is present in an amount ranging from 0.1% to 35% by weight, relative to the total weight of the composition.

41. The anhydrous composition according to claim 40, wherein the at least one additional filler is present in an amount ranging from 1% to 25% by weight, relative to the total weight of the composition.

42. The anhydrous composition according to claim 1, further comprising a polyurethane powder in an amount ranging from 0.5% to 30% by weight, relative to the total weight of the composition.

43. The anhydrous composition according to claim 1, further comprising a polyurethane powder in an amount ranging from 5% to 15% by weight, relative to the total weight of the composition.

44. The anhydrous composition according to claim 1, further comprising a silsesquioxane powder in an amount ranging from 0.5% to 30% by weight, relative to the total weight of the composition.

45. The anhydrous composition according to claim 1, further comprising a silsesquioxane powder in an amount ranging from 1% to 10% by weight, relative to the total weight of the composition.

46. The anhydrous composition according to claim 1, wherein the total content of pulverulent materials ranges from 20% to 50% by weight, relative to the total weight of the composition.

47. The anhydrous composition according to claim 46, wherein the total content of pulverulent materials ranges from 30% to 40% by weight, relative to the total weight of the composition.

48. The anhydrous composition according to claim 1, further comprising at least one inorganic thickener for an oily phase.

49. The anhydrous composition according to claim 48, wherein the at least one inorganic thickener for an oily phase is chosen from organophilic clays and pyrogenic silicas.

50. The anhydrous composition according to claim 48, wherein the at least one inorganic thickener for an oily phase is present in an amount ranging from 0.5% to 5% by weight, relative to the total weight of the composition.

51. The anhydrous composition according to claim 50, wherein the at least one inorganic thickener for an oily phase is present in an amount ranging from 2% to 4% by weight, relative to the total weight of the composition.

52. The anhydrous composition according to claim 1, further comprising at least one additional cosmetic ingredient chosen from antioxidants, fragrances, preservatives, neutralizing agents, surfactants, sunscreen agents, vitamins, moisturizing agents, self-tanning compounds, and antiwrinkle active principles.

53. The anhydrous composition according to claim 1, wherein the composition is in a form chosen from foundations, eye shadows, blushers, concealers, products for making up the body, make-up bases, mattifying products for the skin, and products for caring for the skin.

54. The anhydrous composition according to claim 1, wherein the composition in the form of a deformable non-fluid gel.

55. A foundation composition comprising an anhydrous composition for making up or caring for the skin, comprising
at least one liquid organic phase comprising at least one non-volatile oil,
at least one amorphous gelling polymer formed by polymerization of an olefin, and poly(methyl methacrylate) particles,
wherein the amount of the at least one non-volatile oil present in the composition is greater than the amount of poly(methyl methacrylate) particles present in the composition.

56. A cosmetic process for making up or for the non-therapeutic treatment of the skin, comprising applying to the skin an anhydrous composition for making up or caring for the skin, comprising
at least one liquid organic phase comprising at least one non-volatile oil,
at least one amorphous gelling polymer formed by polymerization of an olefin, and poly(methyl methacrylate) particles,
wherein the amount of the at least one non-volatile oil present in the composition is greater than the amount of poly(methyl methacrylate) particles present in the composition.

57. A method for producing a make-up having good hold, a soft and/or comfortable feeling on made-up skin, a matte appearance, a homogeneous appearance, and/or a powdery appearance, said method comprising applying to the skin at least one anhydrous composition for making up or caring for the skin, comprising
at least one liquid organic phase comprising at least one non-volatile oil,
at least one amorphous gelling polymer formed by polymerization of an olefin, and poly(methyl methacrylate) particles,
wherein the amount of the at least one non-volatile oil present in the composition is greater than the amount of poly(methyl methacrylate) particles present in the composition, and wherein the make-up produced has at least one property chosen from good hold, a soft and/or comfortable feeling on made-up skin, a matte appearance, a homogeneous appearance, and/or a powdery appearance.

* * * * *